(12) United States Patent
De Boer-Wildschut et al.

(10) Patent No.: US 7,767,862 B2
(45) Date of Patent: Aug. 3, 2010

(54) LIGAND, CATALYST AND PROCESS FOR HYDROFORMYLATION

(75) Inventors: Marijke De Boer-Wildschut, Amsterdam (NL); Manutsavin Charernsuk, Bristol (GB); Cornelia Alida Krom, Amsterdam (NL); Monica Carreira Mendez, Clifton Bristol (GB); Wilhelmus Petrus Mul, Amsterdam (NL); Paul Gerard Pringle, Bristol (GB)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 12/538,524

(22) Filed: Aug. 10, 2009

(65) Prior Publication Data

US 2010/0036171 A1 Feb. 11, 2010

(30) Foreign Application Priority Data

Aug. 11, 2008 (EP) .................. 08162143

(51) Int. Cl.
*C07F 9/02* (2006.01)
*C07C 45/50* (2006.01)
*B01J 31/00* (2006.01)

(52) U.S. Cl. .......................... 568/12; 568/454; 502/162
(58) Field of Classification Search .................. 568/12, 568/454
See application file for complete search history.

(56) References Cited

U.S. PATENT DOCUMENTS

| | | | |
|---|---|---|---|
| 3,369,050 A | 2/1968 | Greene | |
| 3,420,898 A | 1/1969 | Van Winkle | 260/632 |
| 3,440,291 A | 4/1969 | Van Winkle | 260/632 |
| 3,448,157 A | 6/1969 | Slaugh | 260/604 |
| 3,448,158 A | 6/1969 | Slaugh | 260/604 |
| 3,501,515 A | 3/1970 | Van Winkle | 260/439 |
| 5,332,846 A | 7/1994 | Devon et al. | 556/21 |
| 6,809,225 B2 | 10/2004 | Donsbach et al. | 568/707 |
| 7,012,162 B2 | 3/2006 | Mackewitz et al. | 568/454 |
| 7,265,242 B2 | 9/2007 | Drent et al. | 560/232 |

FOREIGN PATENT DOCUMENTS

| | | |
|---|---|---|
| WO | WO0052017 | 9/2000 |
| WO | WO03068719 | 8/2003 |
| WO | WO03068786 | 8/2003 |
| WO | WO0382779 | 10/2003 |
| WO | WO2004054946 | 7/2004 |
| WO | WO2004056732 | 7/2004 |
| WO | WO2004094440 | 11/2004 |
| WO | WO2007003589 | 1/2007 |

*Primary Examiner*—Sikarl A Witherspoon

(57) ABSTRACT

According to the present invention, there is provided an organophosphine ligand comprising a phosphabicyclohydrocarbyl group in which the phosphorus atom is further substituted with a hydrocarbyl or heterohydrocarbyl moiety containing at least one branch at the $\beta$-carbon position. The present invention also provides a catalytic composition for the hydroformylation of an ethylenically unsaturated compound, said catalytic composition comprising i) a source of Group VIII metal cations; and ii) the above ligand. Furthermore, the present invention also provides a process for the hydroformylation of an ethylenically unsaturated compound, said process comprising contacting the ethylenically unsaturated compound with carbon monoxide and hydrogen in the presence the above catalytic composition.

11 Claims, No Drawings

LIGAND, CATALYST AND PROCESS FOR HYDROFORMYLATION

FIELD OF THE INVENTION

The present invention relates to a ligand and a catalyst suitable for use in the hydroformylation of ethylenically unsaturated compounds. It also relates to a process for the hydroformylation of ethylenically unsaturated compounds.

BACKGROUND OF THE INVENTION

Various processes for producing aldehyde and/or alcohol compounds by the reaction of an ethylenically unsaturated compound with carbon monoxide and hydrogen in the presence of a catalyst are known. Typically, these reactions are performed at elevated temperatures and pressures. The aldehyde and alcohol compounds that are produced generally correspond to compounds obtained by the addition of a carbonyl or carbinol group, respectively, to an olefinically unsaturated carbon atom in the starting material with simultaneous saturation of the olefin bond. Isomerization of the olefin bond may take place to varying degrees under certain conditions; thus, as a consequence of this isomerization, a variety of products may be obtained. These processes are typically known as hydroformylation reactions and involve reactions which may be shown in the general case by the following equation:

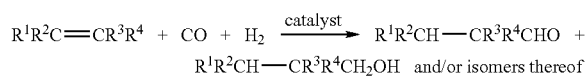

$$R^1R^2C=CR^3R^4 + CO + H_2 \xrightarrow{catalyst} R^1R^2CH-CR^3R^4CHO + R^1R^2CH-CR^3R^4CH_2OH \text{ and/or isomers thereof}$$

In the above equation, each group $R^1$ to $R^4$ may independently represent an organic radical, for example a hydrocarbyl group, or a suitable atom such as a hydrogen or halogen atom, or a hydroxyl group. The above reaction may also be applied to a cycloaliphatic ring having an olefinic linkage, for example cyclohexene.

The catalyst employed in a hydroformylation reaction typically comprises a transition metal, such as cobalt, rhodium or ruthenium, in complex combination with carbon monoxide and ligand(s) such as an organophosphine.

Representative of the earlier hydroformylation methods which use transition metal catalysts having organophosphine ligands are described in U.S. Pat. Nos. 3,420,898, 3,501,515, 3,448,157, 3,440,291, 3,369,050 and 3,448,158.

In attempts to improve the efficiency of a hydroformylation process, attention has typically focussed on developing novel catalysts and novel processes for recovering and re-using the catalyst. In particular, novel catalysts have been developed which may exhibit improved stability at the required high reaction temperatures. Catalysts have also been developed which may permit the single-stage production of alcohols rather than a two-step procedure involving separate hydrogenation of the intermediate aldehyde. Moreover, homogeneous catalysts have been developed which may permit improved reaction rates whilst providing acceptable yields of the desired products.

Phosphabicyclohydrocarbyl ligands are known in the art, and their production and use in hydroformylation reactions are described in many prior art documents, including WO 2004/94440, WO 2003/82779, WO 2003/68719, WO 2003/68786, U.S. Pat. No. 7,012,162, WO 2000/52017, WO 2007/03589, WO 2004/56732 and WO 2004/54946.

Although the use of organophosphine ligands and organophosphine-modified metal catalysts provide very good results in the hydroformylation of ethylenically unsaturated compounds, the use of such ligands and catalysts is known to lead to the production of paraffins as a by-product. The paraffin by-products have very little commercial value. It would, therefore, be desirable to reduce the amount of paraffin by-products formed in a hydroformylation process. Further, it would be desirable to provide an improvement in the activity or reaction rate of a hydroformylation reaction over that catalysed by known metal catalyst systems.

SUMMARY OF THE INVENTION

According to the present invention, there is provided an organophosphine ligand comprising a phosphabicyclohydrocarbyl group in which the phosphorus atom is further substituted with a hydrocarbyl or heterohydrocarbyl moiety containing at least one branch at the β-carbon position.

The present invention also provides a catalytic composition for the hydroformylation of an ethylenically unsaturated compound, said catalytic composition comprising
i) a source of Group VIII metal cations; and
ii) an organophosphine ligand comprising a phospha bicyclohydrocarbyl group in which the phosphorus atom is further substituted with a hydrocarbyl or heterohydrocarbyl moiety containing at least one branch at the β-carbon position.

Furthermore, the present invention also provides a process for the hydroformylation of an ethylenically unsaturated compound, said process comprising contacting the ethylenically unsaturated compound with carbon monoxide and hydrogen in the presence of a catalytic composition comprising
i) a source of Group VIII metal cations; and
ii) an organophosphine ligand comprising a phospha bicyclohydrocarbyl group in which the phosphorus atom is further substituted with a hydrocarbyl or heterohydrocarbyl moiety containing at least one branch at the β-carbon position.

DETAILED DESCRIPTION OF THE INVENTION

It has now surprisingly been found that the amount of by-product paraffins produced in the hydroformylation reaction of an ethylenically unsaturated compound can be reduced and the reaction rate of such a reaction can be increased by using an organophosphine ligand comprising a phosphabicyclohydrocarbyl group in which the phosphorus atom is further substituted with a hydrocarbyl or heterohydrocarbyl moiety containing a branch at the β-carbon position.

Preferably, the organophosphine ligands of the present invention are of general formula (I):

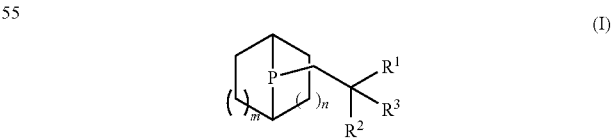

(I)

In general formula (I), m=1, 2 or 3 and n=1, 2 or 3, with the proviso that m+n is less than or equal to 4. That is, the phosphabicyclohydrocarbyl group is selected from the group consisting of 6-phosphabicyclohexyl, 7-phosphabicycloheptyl, 8-phosphabicyclooctyl and 9-phosphabicyclononyl groups, with the proviso that the smallest phosphorus-containing ring in the phosphabicyclohydrocarbyl group contains at least 5 atoms. Any structural isomer of such compounds, e.g. the [3.3.1] and [4.2.1] isomers of a 9-phosphabicyclononyl group, are suitable in the present invention. Preferably, m=2 and n=2 (9-phosphabicyclo[3.3.1]nonyl) or m=3 and n=1 (9-phosphabicyclo[4.2.1]nonyl).

Each carbon atom within the phosphabicyclo hydrocarbyl group may independently be substituted or unsubstituted. Suitable substituents include hydrocarbyl groups, heterohydrocarbyl groups and/or groups comprising heteroatoms.

As used herein, hydrocarbyl refers to groups containing only hydrogen and carbon atoms. Such groups may be saturated or unsaturated, branched or unbranched and may contain aromatic and/or aliphatic moieties.

As used herein, heterohydrocarbyl refers to groups containing hydrogen and carbon atoms as well as heteroatoms. Such groups may be saturated or unsaturated, branched or unbranched and may contain aromatic and/or aliphatic moieties.

Preferably, any substituents on the phospha bicyclohydrocarbyl group carbon atoms are selected from the group consisting of alkyl groups, halogen atoms and groups of general formulae =O, =S, —OH, —OR$^4$, —COR$^4$, —C(O)—OR$^4$, —SH, —SR$^4$, —C(O)—SR$^4$, —NH$_2$, —NHR$^4$, —NR$^4$R$^5$, —NO$_2$, —CN, —C(O)—NH$_2$, —C(O)—NHR$^4$, —C(O)—NR$^4$R$^5$ and Cl$_3$, in which R$^4$ and R$^5$ independently represent alkyl groups having from 1 to 4 carbon atoms, such as methyl, ethyl, n-propyl, isopropyl, n-butyl, iso-butyl and t-butyl.

Preferably, if the phosphabicyclohydrocarbyl ring is substituted it is substituted with one or more alkyl groups, preferably having from 1 to 10 carbon atoms, more preferably from 1 to 4 carbon atoms. Linear, branched or cyclic alkyl groups can be used. Suitable alkyl groups include, methyl, ethyl, propyl, iso-propyl, butyl and iso-butyl. More suitably methyl groups are used. The substituted phosphabicyclohydrocarbyl ring can be mono- or poly-substituted and is preferably di-substituted. Most preferably, if the phosphabicyclohydrocarbyl ring is substituted, it is substituted with two methyl groups.

In one preferred embodiment of the present invention, the phosphabicyclohydrocarbyl group is unsubstituted.

In the present invention, the organophosphine ligand is also substituted on the phosphorus atom by a group containing a branch at the β-carbon position and preferably the organophosphine ligand is of general formula (I). Referring to general formula (I), R$^1$ and R$^2$ may be any suitable hydrocarbyl or heterohydrocarbyl group and not hydrogen and R$^3$ may be any suitable hydrocarbyl or heterohydrocarbyl group or hydrogen.

Suitable groups for R$^1$, R$^2$ and/or R$^3$ include alkyl groups containing in the range of from 1 to 20 carbon atoms.

Substituents on the alkyl groups, if present, may include heteroatoms and heterohydrocarbyl moieties. Preferably, substituents are selected from the group consisting of halogen atoms and groups of general formulae =O, =S, —OH, —OR$^4$, —COR$^4$, —C(O)—OR$^4$, —SH, —SR$^4$, —C(O)—SR$^4$, —NH$_2$, —NHR$^4$, —NR$^4$R$^5$, —NO$_2$, —CN, —C(O)—NH$_2$, —C(O)—NHR$^4$, —C(O)—NR$^4$R$^5$ and Cl$_3$, in which R$^4$ and R$^5$ independently represent alkyl groups having from 1 to 4 carbon atoms, such as methyl, ethyl, n-propyl, isopropyl, n-butyl, iso-butyl and t-butyl.

Alternatively, the branch at the β-carbon position in the organophosphine ligand may take the form of a ring. Said ring may be aliphatic, heteroaliphatic, aromatic or heteroaromatic. Preferably, the ring contains 5 to 10, more preferably 5 to 8 ring atoms. In this embodiment, the organophosphine ligand of the present invention may be more easily represented by the general formula (II):

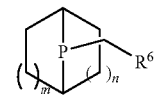

(II)

wherein m, n and the phosphabicyclohydrocarbyl group are as defined above and R$^6$ is a cyclic group. It will be clear to the skilled person that, if R$^6$ is a cyclic group, the organophosphine ligand will be branched at the β-carbon position relative to the phosphorus atom in the phosphabicyclohydrocarbyl group.

R$^6$ may be selected from cyclic groups containing one ring or more than one ring. Preferably, the cyclic group will be monocyclic, i.e. it will contain one ring. R$^6$ preferably consists of a ring having in the range of from 5 to 9, preferably from 5 to 8 ring atoms. The ring atoms are comprised of carbon and, optionally, one or more of oxygen, nitrogen and sulfur. The rings may be aromatic or aliphatic. More preferably, R$^6$ will be selected from the group consisting of cyclopentanes, cyclohexanes, cycloheptanes, cyclooctanes, cyclononanes, benzenes, furans, tetrahydrofurans, tetrahydropyrans, pyrroles, pyridines, thiophenes, oxazoles, imidazoles, thiazoles, isoxazoles, pyrazoles, isothiazoles, oxadiazoles and triazoles.

If chemically possible, any carbon or nitrogen atom in the ring may be substituted with a substituent selected from the group consisting of alkyl groups, halogen atoms and groups of general formulae =O, =S, —OH, —OR$^4$, —COR$^4$, —C(O)—OR$^4$, —SH, —SR$^4$, —C(O)—SR$^4$, —NH$_2$, —NHR$^4$, —NR$^4$R$^5$, —NO$_2$, —CN, —C(O)—NH$_2$, —C(O)—NHR$^4$, —C(O)—NR$^4$R$^5$ and Cl$_3$, in which R$^4$ and R$^5$ independently represent alkyl groups having from 1 to 4 carbon atoms, such as methyl, ethyl, n-propyl, isopropyl, n-butyl, iso-butyl and t-butyl.

In the catalyst and the process of the present invention, suitable Group VIII metals (as used herein the terminology 'Group VIII' is according to 'previous IUPAC form', the Periodic Table of the Elements as published in R C Weast (Ed,) "Handbook of Chemistry and Physics", 54$^{th}$ edition, CRC Press, inside cover) are cobalt, rhodium, ruthenium, nickel, palladium and platinum. Preferably, the Group VIII metal is cobalt.

Cobalt hydroformylation catalysts according to the present invention can be prepared by a diversity of methods well known to those skilled in the art as disclosed in U.S. Pat. Nos. 3,369,050, 3,501,515, 3,448,157, 3,420,898 and 3,440,291, which are all herein incorporated by reference. A convenient method is to combine a cobalt salt, organic or inorganic, with the desired phosphine ligand, for example, in liquid phase followed by reduction and carbonylation. Suitable cobalt salts comprise, for example, cobalt carboxylates such as acetates, octanoates, etc. as well as cobalt salts of mineral acids such as chlorides, fluoride, sulfates, sulfonates, etc. as well as mixtures of one or more of these cobalt salts. The valence state of the cobalt may be reduced and the cobalt-containing complex formed by heating the solution in an atmosphere of hydrogen and carbon monoxide. The reduction may be performed prior to the use of the organophosphine modified cobalt hydroformylation catalysts or it may be accomplished in-situ with the hydroformylation process in the hydroformylation environment. Alternatively, the organophosphine modified cobalt hydroformylation catalysts can be prepared from a carbon monoxide complex of cobalt. For example, it is possible to start with dicobalt octacarbonyl and, by mixing this substance with a suitable phosphine ligand, the ligand replaces one or more of the carbon monoxide molecules, producing an organophosphine modified cobalt hydroformylation catalyst; the active catalyst compound is typically formed under process conditions.

The ethylenically unsaturated compound, used as starting material in the process of the present invention, is preferably an ethylenically unsaturated compound having from 2 to 40 carbon atoms per molecule, or a mixture thereof. Preferred are compounds having from 2 to 30 carbon atoms, or mixtures thereof. The advantages of the process according to the invention are further especially pronounced for larger ethylenically unsaturated compounds comprising at least 4 carbon atoms, and preferably at least 6 carbon atoms. More preferably such a large ethylenically unsaturated compound comprises 8 or more carbon atoms, preferably from 8 to 25 and more preferably from 8 to 18 carbon atoms. The ethylenically unsaturated compound can further be a straight carbon chain or can be branched. Suitable ethylenically unsaturated compounds hence include substituted compounds. Preferably such substituents are alkyl groups, preferably alkyl groups comprising from 1 to 6, more preferably from 1 to 4 carbon atoms, such as methyl, ethyl, n-propyl, isopropyl, n-butyl, iso-butyl and tert-butyl. Examples of suitable ethylenically unsaturated compounds include ethene, propene, butene, pentene, 1-hexene, internal hexenes, 1-heptene, internal heptenes, 1-octene, internal octenes, 1-nonene or internal nonenes, 1-decene or internal decenes, undecenes, methyl-branched undecenes, dodecenes, methyl-branched dodecenes, methyl-substituted or unsubstituted $C_{13}$, $C_{14}$, $C_{16}$, $C_{17}$, $C_{18}$, $C_{19}$ or $C_{20}$-olefins and mixtures of those.

The process is further suitable for the hydroformylation of mono-alkenes in the presence of dienes.

The ethylenically unsaturated compound can further be an ethylenically unsaturated compound comprising functional groups or heteroatoms, such as nitrogen, sulphur or oxide. Examples include unsaturated carboxylic acids, esters of such acids or alkene nitriles. Suitable ethylenically unsaturated compounds comprising functional groups or heteroatoms include, for example, pentene nitriles and methyl-pentenoates.

Preferably, however, the ethylenically unsaturated compound does not comprise any functional groups or heteroatoms and is an olefin comprising only carbon atoms.

In the process of the invention, the unsaturated starting material and the formed product may act as reaction diluent. Hence, the use of a separate solvent is not necessary. Conveniently, however, the hydroformylation reaction may be carried out in the additional presence of a solvent which is inert, or which does not interfere to any substantial degree with the desired hydroformylation reaction under the conditions employed. Saturated liquid hydrocarbons, for example, may be used as solvent in the process, as well as alcohols, ethers, acetonitrile, sulfolane, and the like. Alternatively, a part of an alcoholic reaction product may, if desired, be recycled to the reaction zones to function as solvent and/or diluent and/or suspending medium for the catalyst, the catalyst components, and the like.

Admixtures of promoters and/or stabilizers and the like may also be included in the process of the present invention. Thus, minor amounts of phenolic stabilizers such as hydroquinone and/or alkaline agents such as hydroxides of alkali metals, for example NaOH and KOH, may be added into the process.

The quantity in which the catalyst system is used, is not critical and may vary within wide limits. Usually amounts in the range of $10^{-8}$ to $10^{-1}$, preferably in the range of $10^{-7}$ to $10^{-2}$ mole atom of Group VIII metal per mole of ethylenically unsaturated compound are used. The amounts of the participants in the catalyst system are conveniently selected such that per mole atom of Group VIII metal from 0.1 to 10, preferably from 0.5 to 6, and more preferably from 0.5 to 3 moles of organophosphine are used Carbon monoxide partial pressures in the range of from 1 to 65 bar are preferred. In the process according to the present invention, the carbon monoxide can be used in its pure form or diluted with an inert gas such as nitrogen, carbon dioxide or noble gases such as argon.

For hydroformylation the co-reactant can be molecular hydrogen, or more generally a hydride source. The carbon monoxide and hydrogen are preferably supplied in a molar ratio of hydrogen to carbon monoxide within the range of 10:1 to 1:5, preferably 6:1 to 1:3. The molar ratio of hydrogen to carbon monoxide can influence the type of product prepared. When the desired product is an alkanol, an excess of hydrogen is needed to enable the hydrogenation of the originally formed aldehyde or ketone. Therefore, if the desired product is an alkanol, preferably a molar ratio of hydrogen to carbon monoxide within the range of 4:1 to 1.3:1 is used.

The process of the present invention may be carried out over a wide range of temperatures. Suitable temperatures for the reaction environment are in the range of from 130 to 220° C., preferably in the range of from 140 to 210° C., more preferably in the range of from 150 to 205° C.

The process of the present invention may be carried out at various pressures. Consequently, hydroformylation in accordance with the process of the present invention may typically be carried out at pressures below $8 \times 10^6$ Pa, to as low as $1 \times 10^5$ Pa. The process of the present invention is, however, not limited in its applicability to the lower pressures. Pressures in the broad range of from $1 \times 10^5$ Pa up to about $2 \times 10^7$ Pa, and in some cases up to about $2 \times 10^8$ Pa or higher, may be employed. Typically, the specific pressure used will be governed to some extent by the specific charge and catalyst employed. In general, pressures in the range of from about $2 \times 10^6$ Pa to $10 \times 10^6$ Pa and particularly in the range of from about $2.7 \times 10^6$ Pa to about $9 \times 10^6$ Pa are preferred.

The following non-limiting Examples will illustrate the invention.

EXAMPLES

The Examples were carried out according to the following general procedure:

An autoclave was filled with solvent (2-ethylhexanol), a mixture of C11 and C12 olefins and KOH (K/Co=approx. 0.5). The mixture was heated to approx. 190° C. and a pressure of 50 bars syngas (at a $H_2$:CO ratio of approximately 1.8:1) was applied. A catalyst solution, containing Co(2-ethylhexanoate)$_2$ and a phosphine ligand (at a ratio of P:Co of 1.5:1) in 2-ethylhexanol, was injected into the autoclave. The cobalt concentration in the reaction mixture was 0.11 wt %. The reaction was followed for 6 hours and samples were taken at regular intervals. The results obtained are shown in Table 1.

TABLE 1

| No. | Ligand | *Paraffin make (wt %) | Linearity (%) | k @ 30 min |
|---|---|---|---|---|
| 1** | Phobane-$C_{20}H_{41}$ | 7.5-8.8 | 79.1-81.0 | 0.9-1.1 |
| 2 | Phobane-$CH_2$-THF | 7.1-7.3 | 75.1-76.5 | 1.3-1.5 |
| 3 | Phobane-$CH_2CH(CH_3)_2$ | 5.3-6.6 | 71.1-71.2 | 1.4-1.5 |
| 4 | Phobane-$CH_2$-cyclohexane | 7.5 | 75.8 | 1.2 |
| 5 | Phobane-$CH_2$-tetrahydropyran | 7.9 | 76.8 | 1.2 |

TABLE 1-continued

| No. | Ligand | *Paraffin make (wt %) | Linearity (%) | k @ 30 min |
|---|---|---|---|---|
| 6 | Phobane-CH$_2$-pyridine | 5.2 | 49.1 | 2.1 |

*measured after 6 hours
**comparative example

The invention claimed is:

1. An organophosphine ligand comprising a phosphabicyclohydrocarbyl group in which the phosphorus atom is further substituted with a hydrocarbyl or heterohydrocarbyl moiety containing at least one branch at the β-carbon position.

2. The organophosphine ligand of claim 1 wherein the ligand is of general formula (I):

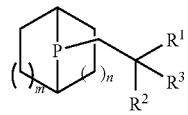

(I)

wherein m=1, 2 or 3 and n=1, 2 or 3, with the proviso that m+n≦4, wherein R$^1$ and R$^2$ are each, independently selected from the group consisting of hydrocarbyl and heterohydrocarbyl groups, and wherein R$^3$ is selected from the group consisting of hydrocarbyl groups, heterohydrocarbyl groups and hydrogen.

3. The organophosphine ligand of claim 2 wherein m=3 and n=1, or where m=2 and n=2.

4. The organophosphine ligand of claim 3 wherein R$^1$ and R$^2$ are each, independently, alkyl groups and R$^3$ is hydrogen.

5. The organophosphine ligand of claim 1 wherein the organophosphine ligand is of general formula (II)

(II)

wherein m=1, 2 or 3 and n=1, 2 or 3, with the proviso that m+n≦4 and R$^6$ is a cyclic group.

6. The organophosphine ligand of claim 5 wherein m=3 and n=1, or where m=2 and n=2.

7. The organophosphine ligand of claim 6 wherein R$^1$ and R$^2$ are each, independently, alkyl groups and R$^3$ is hydrogen.

8. A catalytic composition for the hydroformylation of an ethylenically unsaturated compound, said catalytic composition comprising
    i) a source of Group VIII metal cations; and
    ii) the organophosphine ligand of claim 1.

9. The catalyst of claim 8 wherein the group VIII metal is cobalt.

10. A process for the hydroformylation of an ethylenically unsaturated compound, said process comprising contacting the ethylenically unsaturated compound with carbon monoxide and hydrogen in the presence of a catalytic composition comprising
    i) a source of Group VIII metal cations; and
    ii) the organophosphine ligand of claim 1.

11. The process of claim 10 wherein the ethylenically unsaturated compound is a mono-alkene.

* * * * *